United States Patent [19]

Böhshar et al.

[11] Patent Number: 5,356,967
[45] Date of Patent: Oct. 18, 1994

[54] 6-ARYL-6H-DIBENZO[C,E][1,2]OXAPHOS-PHORINE STABILIZERS FOR PLASTICS

[75] Inventors: Manfred Böhshar, Kelkheim/Taunus; Hans-Jerg Kleiner, Kronberg/Taunus; Gerhard Pfahler, Augsburg, all of Fed. Rep. of Germany

[73] Assignee: Hoechst Aktiengesellschaft, Frankfurt, Fed. Rep. of Germany

[21] Appl. No.: 962,187
[22] PCT Filed: Jun. 22, 1991
[86] PCT No.: PCT/EP91/01158
 § 371 Date: Dec. 23, 1992
 § 102(e) Date: Dec. 23, 1992
[87] PCT Pub. No.: WO92/00306
 PCT Pub. Date: Jan. 9, 1992

[30] Foreign Application Priority Data

Jul. 2, 1990 [DE] Fed. Rep. of Germany ....... 4021195
Jun. 3, 1991 [DE] Fed. Rep. of Germany ....... 4118147

[51] Int. Cl.⁵ .................. C07B 49/00; C07F 9/6574; C08K 5/5377
[52] U.S. Cl. .................... 524/117; 558/82; 558/134
[58] Field of Search .............. 558/82, 134; 524/117; 430/551, 372

[56] References Cited

U.S. PATENT DOCUMENTS

| | | | |
|---|---|---|---|
| 3,702,878 | 11/1972 | Saito et al. | 524/117 |
| 4,185,006 | 1/1980 | Rasberger et al. | 524/117 |
| 4,406,842 | 9/1983 | Spivack | 260/962 |
| 4,474,914 | 10/1984 | Spivack | 524/126 |
| 4,732,997 | 3/1988 | Tschopp et al. | 558/82 |
| 5,008,426 | 4/1991 | Kleiner et al. | 558/82 |
| 5,109,043 | 4/1992 | Bohshar et al. | 558/134 |
| 5,128,495 | 7/1992 | Scheffel et al. | 558/134 |

FOREIGN PATENT DOCUMENTS 60-163890 8/1985 Japan.

OTHER PUBLICATIONS

Houben-Weyl's *Methods of Organic Chemistry*, 4th Ed'n., vol. XII/1, Stuttgart, Germany, Georg Thieme Verlag, 1963, pp. 208–211, 221, 296.
*Encyclopedia of Polymer Science and Engineering*, Rev. Ed., John Wiley & Sons, Inc. 1985, p. 87.
*Polymer Additives, Guidebook and Directory*, Noyes Data Corporation, Park Ridge, N.J., 1972, pp. 127–128.
Nippon Ester Co., Ltd., *Patent Abs. of JP* 132:61-266614 (1985), abstract of JP 61-266614, Nov. 26, 1986.

*Primary Examiner*—Veronica P. Hoke
*Attorney, Agent, or Firm*—Connolly and Hutz

[57] ABSTRACT

A dibenzo-[c,e] [1,2] oxaphorine of the formula I and process of making said compound

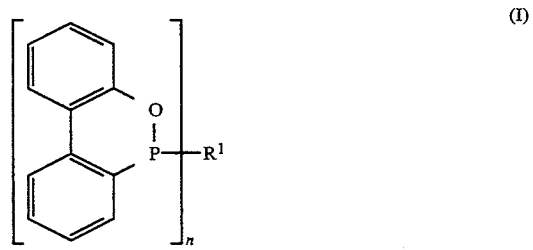

wherein n=1 or 2 and in which $R^1$ is a monovalent or divalent aromatic radical wherein a Grignard compound $R^1(MgHal)_n$ is reacted with 6-chloro-6H-dibenzo[c,e][1,2] oxaphosphorine.

This compound optionally with phenolic antioxidants, provides stabilization in polymers.

16 Claims, No Drawings

6-ARYL-6H-DIBENZO[C,E][1,2]OXAPHOSPHORINE STABILIZERS FOR PLASTICS

The present invention relates to novel 6-aryl-6H-dibenzo-[c,e][1,2]oxaphosphorines, to a process for their preparation, and to their use for stabilizing plastics, in particular polyolefins.

It is known that synthetic polymers must be protected by stabilizers or stabilizer systems against undesired oxidative, thermal and photochemical damage during preparation, processing and use. Such stabilizers comprise, for example, a phenolic antioxidant, which is intended, in particular, to ensure the running time stability in use of the finished part, and one or more costabilizers, which regulate the processing stability and in some cases also synergistically increase the action of the phenolic component.

Conventional costabilizers include, for example, ortho-alkylated aryl phosphites and phosphonites.

Although the diaryl phosphonites described in European Patent 5 447 have adequate properties as stabilizers for certain areas of application, their synthesis starts from organodichlorophosphines which are poorly accessible in industry. In practice, the only industrially available precursor is dichlorophenylphosphine, which is the only possible precursor to derivatives of benzenephosphonous acid. However, to achieve the desired properties, it is frequently desirable to have precisely compounds containing higher substituted aryl groups on the phosphorus available.

A further serious disadvantage is the necessity to neutralize hydrogen chloride liberated during the synthesis by means of a suitable auxiliary base. In the recycling thereof, the inevitable formation of two equivalents of the corresponding salt is unavoidable.

The phosphonites prepared in German Offenlegungsschrift 2 034 887 by hydrolysis, esterification, transesterification, alkylation or sulfation of 6-chlorodibenzo[c,e][1,2]oxaphosphorine have, inter alia, disadvantages with respect to shelf life, color behavior and hydrolysis resistance, as has already been described in U.S. Pat. No. 4,185,006.

The object of the present invention was therefore to provide novel phosphorus stabilizers which, on the one hand, satisfy the high demands of practice and in particular do not decompose into a plurality of fragments and/or acidic secondary products, even on contact with water, but at the same time can be prepared simply and in high yield by ecologically favorable processes.

Surprisingly, it has now been found that cyclic phosphinous acid esters of the formula I

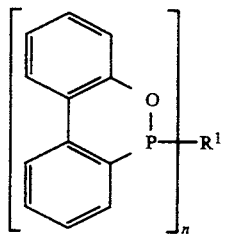

(I)

meet these requirements very well.

The invention thus relates to dibenzo[c,e][1,2]oxaphosphorines of the formula I, i.e. aryl-6H-dibenzo[c,e][1,2]oxaphosphorines where n=1 and arylbis{6H-dibenzo[c,e][1,2]oxaphosphorines} where n=2, in which $R^1$, as a monovalent radical, is a phenyl radical, which may carry 1 to 3 substituents, or a naphthyl radical, which may carry 1 to 5 substituents, the substituents being identical or different nonaromatic hydrocarbon, alkoxy, alkylthio or dialkylamino radicals, in each case having 1 to 8 carbon atoms, aryl or aryloxy, in each case having 6 to 10 carbon atoms, or halogen having an atomic number of from 9 to 35, or, as a divalent radical, is a phenylene or biphenylene radical which is unsubstituted or substituted by up to 4 nonaromatic hydrocarbon radicals having 1 to 8 carbon atoms, or is a naphthylene radical which is unsubstituted or carries 1 to 4 nonaromatic hydrocarbon radicals having 1 to 8 carbon atoms as substituents.

Specific examples of $R^1$ as a monovalent radical are the various tolyl radicals, xylyl radicals, mesityl, 2,4,5-trimethylphenyl, the various tert.-butylphenyl radicals, di-tert.-butylphenyl radicals, 2,4,6-tri-tert.-butylphenyl, 2,4-di-tert.-octylphenyl, and the various biphenyl, methylnaphthyl, dimethylnaphthyl and trimethylnaphthyl radicals.

Specific examples of $R^1$ as a divalent radical are the various phenylene radicals, such as 1,3- and 1,4-phenylene, the various biphenylene radicals, such as 2',3-, 2',4-, 3',3-, 3',4- and 4,4'-biphenylene, and the various naphthylene radicals, such as 1,4- and 1,6-naphthylene.

The invention also relates to a process for the preparation of the phosphinous acid esters of the formula I in which $R^1$ is as defined above, which comprises firstly, in a first step, reacting a hydrocarbon halide $R^1$-$(Hal)_n$ in which $R^1$ is as defined above, n=1 or 2, and the halogen has an atomic weight of at least 35, but is preferably chlorine or bromine, under Grignard conditions, i.e. expediently with intimate mixing, with an at least stoichiometric amount of finely divided magnesium to give the corresponding Grignard compound $R^1(MgHal)_n$, and reacting the latter, in a second step, with 6-chloro-6H-dibenzo[c,e][1,2]oxaphosphorine.

The first step of the process according to the invention, which can in principle be carried out in any conventional manner, is preferably carried out in an aprotic, organic solvent, such as an ether, for example diethyl ether, dipropyl ether or diisopropyl ether, ethylene glycol dimethyl ether, ethylene glycol diethyl ether, diethylene glycol dimethyl ether, diethylene glycol diethyl ether, methyl tert.-butyl ether, dioxane or tetrahydrofuran.

Since the Grignard compounds are sensitive to hydrolysis and oxidation, it may be expedient to work under a protective-gas atmosphere. However, a procedure of this type is in no way essential for the success of the reaction. Particularly suitable protective gases are nitrogen and argon. The reaction temperature is generally between 20° and 125° C., but preferably between 30° and 70° C. The use of ultrasound during the formation of the Grignard compound is sometimes advantageous.

To prepare the compounds I, the solution or suspension of the Grignard reagent is reacted in the second step with a solution of 6-chloro-6H-dibenzo[c,e][1,2]oxaphosphorine. This may be carried out, for example, by metering the solution or suspension of the Grignard reagent into a solution of 6-chloro-6H-dibenzo[c,e][1,2]oxaphosphorine with vigorous mixing. However, the reverse addition is also possible. Suitable diluents are inert, aprotic solvents, for example an aliphatic hydrocarbon fraction, hexane, heptane, cyclohexane, toluene, xylene or one of the abovementioned ethers, or appropriate mixtures. The reaction temperature in this stage is generally between −30° and +50° C., but preferably between −20° and +20° C. The reaction is generally exothermic; it may accordingly be expedient to control the course of the reaction by cooling. The most favorable results are achieved if the reactants are employed in stoichiometric amounts. However, it is also possible to employ one reactant in excess; however, this is generally not associated with any particular advantages. The mixture is expediently stirred until the reaction is complete, and precipitated magnesium halide is subsequently separated off. The solvents can be removed from the filtrate in a conventional manner, advantageously by distillation, in particular under reduced pressure.

The products I can be isolated from the crude products by any desired method, but preferably by crystallization.

In the synthesis of phosphinous acid esters by reacting phosphorous acid ester halides with organomagnesium halides, a yield-reducing side reaction is the replacement of the OR radical by the Grignard compound, so that even in the most favorable cases, the yields achieved do not exceed 60% (Houben-Weyl: "Methoden der organischen Chemie" [Methods of Organic Chemistry], 12/1, p. 210 (1963)).

In addition, there was a prejudice in the literature along the lines that the reaction of phosphonous acid halides with organomagnesium bromides always initially gives insoluble complex compounds, which must first be broken down by adding further assistants (for example 4 mol of pyridine) in order to facilitate isolation of the desired phosphinous acid esters (Houben-Weyl, loc. cit.). It is therefore particularly surprising that the process of the present invention gives the phosphinous acid esters I in high yield and purity without the use of decomplexing agents being necessary.

The 6-chloro-6H-dibenzo[c,e][1,2]oxaphosphorine required as a precursor is accessible in a simple manner by the process of German Offenlegungsschrift 2 034 887 from phosphorus trichloride and o-phenylphenol without the use of a solvent or auxiliary base.

The invention finally relates to the use of the compounds of the formula V, alone or in combination with a phenolic antioxidant, for stabilizing plastics, such as polycarbonates, preferably polymerization plastics such as polyolefins, in particular polypropylene. The compounds of the formula I improve the stability of the plastics in the molding compositions against degradation by light, oxygen and heat. However, the purity of the crude reaction product obtained (85–93% according to $^{31}$P-NMR) is frequently adequate for this application. Isolation in pure form is then unnecessary.

The present invention thus also relates to a plastic molding composition containing a thermoplastic or thermoset and a 6-aryl-6H-dibenzo[c,e][1,2]oxaphosphorine of the formula I in a ratio of from (90 to 99.99):(0.01 to 10), where n=1 or 2 and in which $R^1$, as a monovalent radical, is a phenyl radical, which may carry 1 to 3 substituents, or a naphthyl radical, which may carry 1 to 5 substituents, the substituents being identical or different nonaromatic hydrocarbon, alkoxy, alkylthio or dialkylamino radicals, in each case having 1 to 8 carbon atoms, aryl or aryloxy, in each case having 6 to 10 carbon atoms, or halogen having an atomic number of from 9 to 35, or, as a divalent radical, is a phenylene or biphenylene radical which is unsubstituted or substituted by up to 4 nonaromatic hydrocarbon radicals having 1 to 8 carbon atoms, or is a naphthylene radical which is unsubstituted or carries 1 to 4 nonaromatic hydrocarbon radicals having 1 to 8 carbon atoms as substituents.

The plastic molding composition according to the invention contains a thermoplastic or thermoset organic polymer, for example one of the polymers listed below:

1. Polymers of mono- or diolefins, for example high-, medium- or low-density polyethylene (which may, if desired, be crosslinked), polypropylene, polyisobutylene, poly-1-butene, polymethyl-1-pentene, polyisoprene or polybutadiene, and polymers of cycloolefins, such as cyclopentene or norbornene.
2. Mixtures of the polymers mentioned under 1), for example of polypropylene and polyethylene or polyisobutylene.
3. Copolymers of mono- or diolefins with one another or with other vinyl monomers, such as ethylene-propylene copolymers, propylene-1-butene copolymers, propylene-isobutylene copolymers, ethylene-1-butene copolymers, propylene-butadiene copolymers, isobutylene-isoprene copolymers, ethylene-alkyl acrylate copolymers, ethylene-alkyl methacrylate copolymers, ethylene-vinyl acetate copolymers or ethylene-acrylic acid copolymers, and salts thereof (ionomers), and terpolymers of ethylene with propylene and a diene, such as hexadiene, dicyclopentadiene or ethylidenenorbornene.
4. Polystyrene.
5. Copolymers of styrene or α-methylstyrene with dienes or acrylic derivatives, such as styrene-butadiene, styrene-maleic anhydride, styrene-acrylonitrile, styrene-ethyl methacrylate, styrene-butadiene-ethyl acrylate and styrene-acrylonitrile-methyl acrylate; mixtures of high impact strength made from styrene copolymers and another polymer, such as a polyacrylate, a diene polymer or an ethylene-propylene-diene terpolymer; and block copolymers of styrene, such as styrene-butadiene-styrene, styrene-isoprene-styrene, styrene-ethylene/butylene-styrene or styrene-ethylene/-propylene-styrene.
6. Graft copolymers of styrene, such as styrene on polybutadiene, styrene and acrylonitrile on polybutadiene (ABS), styrene and maleic anhydride on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, and mixtures thereof with the copolymers mentioned under 5), which are known, for example, as ABS, MBS, ASA or AES polymers.
7. Halogen-containing polymers, such as polychloroprene, chlorinated rubber, chlorinated (CPE) or chlorosulfonated polyethylene, epichlorohydrin homopolymers and copolymers, in particular polymers of halogen-containing vinyl compounds, such as polyvinyl chloride (PVC), polyvinylidene chloride (PVDC), polyvinyl fluoride and polyvinylidene fluoride (PVDF); and copolymers thereof, such as vinyl chloride-vinylidene chloride, vinyl chloride-vinyl acetate or vinylidene chloride-vinyl acetate.
8. Polymers derived from α,β-unsaturated carboxylic acids and derivatives thereof, such as polyacrylates and polymethacrylates, polyacrylamides and polyacrylonitriles.

9. Copolymers of the monomers mentioned under 8) with one another or with other unsaturated monomers, such as acrylonitrile-butadiene copolymers, acrylonitrile-alkyl acrylate copolymers, acrylonitrile-alkoxyacrylate copolymers, acrylonitrile-vinyl halide copolymers or acrylonitrile-alkyl methacrylate-butadiene terpolymers.

10. Polymers derived from unsaturated alcohols and amines or acyl derivatives or acetals thereof, such as polyvinyl alcohol, polyvinyl acetate, polyvinyl stearate, polyvinyl benzoate, polyvinyl maleate, polyvinylbutyral, polyallyl phthalate and polyallylmelamine.

11. Homopolymers and copolymers of cyclic ethers, such as polyethylene glycols, polyethylene oxide, polypropylene oxide or copolymers thereof with bisglycidyl ethers.

12. Polyacetals, such as polyoxymethylene (POM), and polyoxymethylenes containing comonomers such as ethylene oxide.

13. Polyphenylene oxides and sulfides.

14. Polyurethanes (PUR) derived on the one hand from polyethers, polyesters and polybutadienes containing terminal hydroxyl groups and on the other hand from aliphatic or aromatic polyisocyanates, and precursors thereof (polyisocyanate-polyol prepolymers).

15. Polyamides and copolyamides derived from diamines and dicarboxylic acids and/or from aminocarboxylic acids or the corresponding lactams, such as nylon 4, nylon 6, nylon 6/6, nylon 6/10, nylon 11, nylon 12, poly-2,4,4-trimethylhexamethylene terephthalamide, poly-m-phenylene isophthalamide, and copolymers thereof with polyethers, such as with polyethylene glycol, polypropylene glycol or polytetramethylene glycol.

16. Polyureas, polyimides and polyamide-imides.

17. Polyesters derived from dicarboxylic acids and diols and/or from hydroxycarboxylic acids or the corresponding lactones, such as polyethylene terephthalate, polybutylene terephthalate (PBTP), poly-1,4-dimethylolcyclohexane terephthalate, poly(2,2-bis(4-hydroxyphenyl)propane) terephthalate, polyhydroxybenzoates, and block polyetheresters derived from polyethylene containing hydroxyl end groups, dialcohols and dicarboxylic acids.

18. Polycarbonates (PC).

19. Polysulfones and polyether sulfones.

20. Crosslinked polymers derived on the one hand from aldehydes and on the other hand from phenols, urea or melamine, such as phenol-formaldehyde, urea-formaldehyde and melamine-formaldehyde resins.

21. Drying and nondrying alkyd resins.

22. Unsaturated polyester resins derived from copolyesters of saturated and unsaturated dicarboxylic acids with polyhydric alcohols, and vinyl compounds as crosslinking agents, and the halogen-containing, low-combustibility modifications thereof.

23. Crosslinkable acrylic resins derived from substituted acrylates, such as from epoxy acrylates, urethane acrylates or polyester acrylates.

24. Alkyd resins, polyester resins and acrylate resins crosslinked with melamine resins, urea resins, polyisocyanates or epoxy resins.

25. Crosslinked epoxy resins derived from polyepoxides, for example from bisglycidyl ethers or from cycloaliphatic diepoxides.

26. Natural polymers, such as cellulose, natural rubber, gelatin and derivatives thereof which have been chemically modified polymer-homologously, such as cellulose acetates, propionates and butyrates, and cellulose ethers, such as methylcellulose.

27. Mixtures of the abovementioned polymers, such as, for example, PP/EPDM, nylon 6/EPDM or ABS, PVC/EVA, PVC/ABS, PVC/MBS, PC/ABS, PBTP/ABS, PC/ASA, PC/PBT, PVC/CPE, PVD/acrylate, POM/thermoplastic PUR, POM/acrylate, POM/MBS, polyphenylene ether/high impact strength polystyrene (PPE-/HIPS), PPE/nylon 6.6 and copolymers, PA/HDPE, PA/PP and PA/PPE.

28. Naturally occurring and synthetic organic substances which are pure monomers or mixtures of monomers, such as mineral oils, animal and vegetable fats, oils and waxes, or oils, fats and waxes based on synthetic esters, or mixtures of these substances.

29. Aqueous dispersions of natural or synthetic rubber.

The polymer is preferably a polyolefin, in particular polypropylene. The proportion of the polymer in the molding composition according to the invention is from 90 to 99.99% by weight, preferably from 98 to 99.98% by weight.

The molding composition contains, as stabilizer, an oxaphosphorine of the formula I and, if desired, a phenolic antioxidant.

The phenolic antioxidant is, for example, an ester of 3,3-bis(3'-t-butyl-4'-hydroxyphenyl)butanoic acid of the formula II

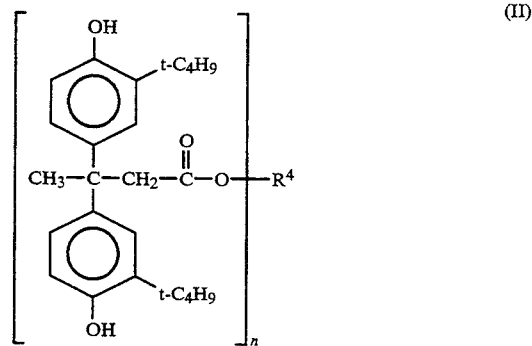

in which n is 1 or 2, and $R^4$ is a $C_1$–$C_{12}$-alkyl radical if n is 1 and a $C_1$–$C_{12}$-alkylene radical if n is 2. $R^4$ is preferably a $C_2$–$C_4$-alkylene radical, in particular a $C_2$-alkylene radical.

However, the phenolic antioxidant may alternatively be an ester of β-(3,5-di-t-butyl-4-hydroxyphenyl) propionic acid of the formula III

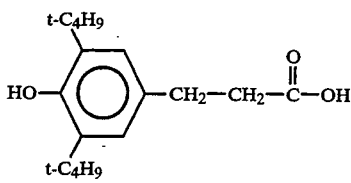

(III)

where the alcohol component is a monohydric to tetrahydric alcohol, such as methanol, octadecanol, 1,6-hexanediol, neopentyl glycol, diethylene glycol, triethylene glycol, pentaerythritol, trishydroxyethyl isocyanurate, thiodiethylene glycol or dihydroxyethyl oxalamide.

The novel stabilizers are incorporated into the organic polymers by generally conventional methods. The incorporation can be effected, for example, [lacuna] by mixing the compounds and, if desired, further additives into the melt before or during molding. The incorporation can also take place by applying the dissolved or dispersed compounds onto the polymer directly or by mixing them into a solution, suspension or emulsion of the polymer, if desired subsequently allowing the solvent to evaporate. The amount to be added to the polymers is from 0.01 to 10% by weight, preferably from 0.025 to 5% by weight, in particular from 0.05 to 1.0% by weight, based on the material to be stabilized.

The novel compounds can also be added to the polymers to be stabilized in the form of a masterbatch, which, for example, contains these compounds in a concentration of from 1 to 50% by weight, preferably from 2.5 to 20% by weight.

In addition, the molding composition according to the invention may also contain other antioxidants, such as 1. Alkylated monophenols, for example 2,6-di-t-butyl-4-methylphenol, -4-ethylphenol, -4-n-butylphenol and -4-i-butylphenol, 2-t-butyl-4,6-dimethylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol and 2,6-di-t-butyl-4-methoxymethylphenol;
2. Alkylated hydroquinones, such as 2,5-di-t-butyl- and 2,5-di-t-amylhydroquinone, 2,6-di-t-butyl-4-methoxyphenol and 2,6-diphenyl-4-octadecyloxyphenol;
3. Hydroxylated thiodiphenyl ethers, such as 2,2′-thiobis(6-t-butyl-4-methylphenol) and -(4-octylphenol), and 4,4′-thiobis(6-t-butyl-3-methylphenol) and -(6-t-butyl-2-methylphenol);
4. Alkylidenebisphenols, such as 2,2′-methylenebis(6-t-butyl-4-methylphenol), -(6-t-butyl-4-ethylphenol), -[4-methyl-6-(α-methylcyclohexyl)-phenol], -(4-methyl-6-cyclohexylphenol), -(6-nonyl-4-methylphenol), -(4,6-di-t-butylphenol), -[6-(α-methylbenzyl)-4-nonylphenol] and -[6-(α,α-dimethylbenzyl)-4-nonylphenol], 4,4′-methylenebis(2,6-di-t-butylphenol) and -(6-t-butyl-2methylphenol), 2,2′-ethylidenebis(4,6-di-t-butylphenol) and -(6-t-butyl-4-isobutylphenol), 1,1-bis and 1,1,3-tris(5-t-butyl-4-hydroxy-2-methylphenyl)butane, 2,6-di-(3-t-butyl-5-methyl-2-hydroxybenzyl)-4- methylphenol, 1,1-bis(5-t-butyl-4-hydroxy-2-methylphenyl)-3-n-dodecylmercaptobutane and di(3-t-butyl-4-hydroxy-5-methylphenyl)dicyclopentadiene;
5. Benzyl compounds, such as di[2-(3′-t-butyl-2′-hydroxy-5′-methylbenzyl)-6-t-butyl-4-methylphenyl] terephthalate, 1,3,5-tri(3,5-di-t-butyl-4-hydroxybenzyl)-2,4,6-trimethylbenzene, di(3,5-di-t-butyl-4-hydroxybenzyl) sulfide, isooctyl 3,5-di-t-butyl-4-hydroxybenzylmercaptoacetate, bis(4-t-butyl-3-hydroxy-2,6-dimethylbenzyl)dithiol terephthalate, 1,3,5-tris(3,5-di-t-butyl-4-hydroxybenzyl) isocyanurate, 1,3,5-tris(4-t-butyl-3-hydroxy-2,6-dimethylbenzyl) isocyanurate, dioctadecyl 3,5-di-t-butyl-4-hydroxybenzylphosphonate and the calcium salt of monoethyl 3,5-di-t-butyl-4hydroxybenzylphosphonate;
6. Acylaminophenols, such as 4-hydroxylauranilide, 4-hydroxystearanilide, 2,4-bisoctylmercapto-6-(3,5-di-t-butyl-4-hydroxyanilino)-s-triazine and octyl N-(3,5-di-t-butyl-4-hydroxyphenyl)carbamate;
7. Esters of β-(5-t-butyl-4-hydroxy-3-methylphenyl)-propionic acid with monohydric or polyhydric alcohols, such as with methanol, octadecanol, 1,6-hexanediol, neopentyl glycol, diethylene glycol, triethylene glycol, pentaerythritol, trishydroxyethyl isocyanurate, thiodiethylene glycol or dihydroxyethyloxalamide;
8. Amides of β-(3,5-di-t-butyl-4-hydroxyphenyl)propionic acid, such as N,N′-di(3,5-di-t-butyl-4-hydroxyphenylpropionyl)trimethylenediamine, -hexamethylenediamine and -hydrazine.

In addition, the molding composition according to the invention may contain further additives, such as 1. UV absorbers and light stabilizers, for example
1.1 2-(2′-Hydroxymethyl)benzotriazoles, such as the 5′-methyl, 3′,5′-di-t-butyl, 5′-t-butyl, 5′-(1,1,3,3-tetramethylbutyl), 5-chloro-3′,5′-di-t-butyl, 5-chloro-3′-t-butyl-5′-methyl, 3′-sec.-butyl-5′-t-butyl, 4′-octoxy, 3′,5′-di-t-amyl and 3′,5′-bis(α,α-dimethylbenzyl) derivatives;
1.2 2-Hydroxybenzophenones, such as the 4-hydroxy, 4-methoxy, 4-octoxy, 4-decyloxy, 4-dodecyloxy, 4-benzyloxy, 4,2′,4′-trihydroxy and 2′-hydroxy-4,4′-dimethoxy derivatives;
1.3 Esters of substituted or unsubstituted benzoic acids, such as phenyl salicylate, 4-t-butylphenyl salicylate, octylphenyl salicylate, dibenzoylresorcinol, bis(4-t-butylbenzoyl)resorcinol, benzoylresorcinol, 2,4-di-t-butylphenyl 3,5-di-t-butyl-4-hydroxybenzoate and hexadecyl 3,5-di-t-butyl-4-hydroxybenzoate;
1.4 Acrylates, such as ethyl and isooctyl α-cyano-β,β-diphenylacrylate, methyl α-carbomethoxy- and α-carbomethoxy-p-methoxycinnamate, methyl and butyl α-cyano-β-methyl-p-methoxycinnamate and N-(β-carbomethoxy-β-cyanovinyl)-2-methylindoline;
1.5 Nickel compounds, such as nickel complexes of 2,2′-thiobis[4-(1,1,3,3-tetramethylbutyl)phenol], such as the 1:1 or 1:2 complex, if desired with additional ligands, such as n-butylamine, triethanolamine or N-cyclohexyldiethanolamine, nickel alkyldithiocarbamates, nickel salts of monoalkyl 4-hydroxy-3,5-di-t-butylbenzylphosphonates, such as of the methyl or ethyl ester, nickel complexes of ketoximes, such as of 2-hydroxy-4-methylphenyl undecyl ketone oxime, [lacuna]and nickel complexes of 1-phenyl-4-llauroyl-5-hydroxypyrazole, if desired with additional ligands;
1.6 Sterically hindered amines, such as
1.6.1. Bis(2,2,6,6-tetramethylpiperidyl) sebacate, glutarate and succinate, bis(1,2,2,6,6-pentamethylpiperidyl) sebacate, glutarate and succinate, 4-stearyloxy- and 4-stearoyloxy-2,2,6,6-tetramethylpiperidine, 4-stearyloxy- and 4-stearoyloxy-1,2,2,6,6-pentamethylpiperidine, 2,2,6,6-tetramethylpiperidyl behenate, 1,2,2,6,6-pentamethyl-piperidyl behenate, 2,2,4,4-tetramethyl-7-oxa-3,20-diazadispiro[5.1.11.2]heneicosan-21-one, 2,2,3,4,4-pentamethyl-7-oxa-3,20-diazadispiro[5.1.11.2-]heneicosan-21-one, 2,2,4,4-tetramethyl-3-acetyl-7-oxa-3,20-diazadispiro[5.1.11.2]heneicosan-21-one, 2,2,4,4-tetramethyl-7-oxa-3,20-diaza-20-($\beta$-lauryloxycarbonylethyl)-21-oxodispiro[5.1.11.2-]heneicosane, 2,2,3,4,4-pentamethyl-7-oxa-3,20-diaza-20-($\beta$-lauryloxycarbonylethyl)-21-oxodispiro[5.1.11.2]heneicosane, 2,2,4,4-tetramethyl-3-acetyl-7-oxa-3,20-diaza-20-($\beta$-lauryloxycarbonylethyl)-21-oxodispiro [5.1.11.2]heneicosane, 1,1',3,3',5,5'-hexahydro-2,2',4,4',6,6'-hexaaza-2,2',6,6'-bismethano-7,8-dioxo-4,4'-bis(1,2,2,6,6-pentamethyl-4-piperidyl)-biphenyl, N,N',N'',N'''-tetrakis{2,4-bis[N-(2,2,6,6-tetramethyl-4-piperidyl)butylamino]-1,3,5-triazin-6yl}-4,7-diazadecane-1,10-diamine, N,N',N'',N'''-tetrakis{2,4-bis[N-(1,2,2,6,6-pentamethyl-4-piperidyl)-butylamino]-1,3,5-triazin-6yl}-4,7-diazadecane-1,10-diamine, N,N',N'',N'''-tetrakis{2,4-bis[N-(2,2,6,6-tetramethyl-4-piperidyl)methoxy-propylamino]-1,3,5-triazin-6-yl}-4,7-diazadecane-1,10-diamine, N,N',N'',N'''-tetrakis-{2,4-bis[N-(1,2,2,6,6-pentamethyl-4-piperidyl)methoxy-propylamino]-1,3,5-triazin-6-yl}-4,7-diazadecane-1,10-diamine, bis(1,2,2,6,6-pentamethylpiperidyl)-n-butyl-3,5-di-tert.-butyl-4-hydroxybenzyl malonate, tris(2,2,6,6-tetramethyl-4-piperidyl) nitrilotriacetate, tetrakis(2,2,6,6-tetramethyl-4-piperidyl)-1,2,3,4-butanetetracarboxylic acid and 1,1'-(1,2-ethanediyl)bis(3,3,5,5-tetramethylpiperazinone).

1.6.2 Poly-N,N'-bis(2,2,6,6-tetramethyl-4-piperidyl)-1,8-diazadecylene, the product of the condensation of 1-(2-hydroxyethyl)-2,2,6,6-tetramethyl-4-hydroxypiperidine and succinic acid, the product of the condensation of N,N'-bis(2,2,6,6-tetramethyl-4-piperidyl)hexamethylenediamine and 4-tert.-octylamino-2,6-dichloro-1,3,5-s-triazine, and the product of the condensation of N,N'-bis(2,2,6,6-tetramethyl-4-piperidyl)hexamethylenediamine and 4-morpholino-2,6-dichloro-1,3,5-triazine.
[lacuna]

In many cases, a combination of the compounds according to the invention has proven particularly advantageous.

1.7 Oxalamides, such as 4,4'-dioctyloxyoxanilide, 2,2'-dioctyloxy-5,5'-di-t-butyloxanilide, 2,2'-didodecyloxy-5,5'-di-t-butyloxanilide, 2-ethoxy-2'-ethyloxanilide, N,N'-bis(3-dimethylaminopropyl)oxalamide, 2-ethoxy-5-t-butyl-2'-ethyloxanilide and the mixture thereof with 2-ethoxy-2'-ethyl-5,4-di-t-butyloxanilide, and mixtures of o- and p-methoxy- and -ethoxy-disubstituted oxanilides;

2. Metal deactivators, such as N,N'-diphenyloxalamide, N-salicylal-N'-salicyloylhydrazine, N,N'-bissalicyloylhydrazine, N,N'-bis(3,5-di-t-butyl-4-hydroxyphenylpropionyl)hydrazine, 3-salicyloylamino-1,2,3triazole and bisbenzylideneoxalodihydrazide;

3. Phosphites and phosphonites, for example triphenyl phosphite, diphenyl alkyl phosphites, phenyl dialkyl phosphites, trisnonylphenyl phosphite, trilauryl phosphite, trioctadecyl phosphite, distearyl pentaerythrityl diphosphite, tris(2,4-di-t-butylphenyl) phosphite, diisodecyl pentaerythrityl diphosphite, bis(2,4-di-t-butylphenyl) pentaerythrityl diphosphite, tristearyl sorbityl triphosphite, tetrakis (2,4-di-t-butylphenyl)-4,4 '-biphenylene diphosphonite, 3,9-bis(2,4-di-t-butylphenoxy)-2,4,8,10-tetraoxa-3,9-diphosphaspiro[5.5]undecane and tris(2-t-butyl-4-thio(2'-methenyl-4'-hydroxy-5'-t-butyl)phenyl-5methenyl)phenyl phosphite.

4. Peroxide-destroying compounds, such as esters of $\beta$-thiodipropionic acid, for example the lauryl, stearyl, myristyl and tridecyl esters, mercaptobenzimidazole, the zinc salt of 2-mercaptobenzimidazole, zinc alkyldithiocarbamates, dioctadecyl sulfide, dioctadecyl monosulfide and pentaerythritol tetrakis($\beta$-dodecylmercapto)propionate;

5. Basic costabilizers, such as melamin, polyvinylpyrrolidone, dicyandiamide, triallyl cyanurate, urea derivatives, hydrazine derivatives, amines, polyamines, polyurethanes, alkali and alkaline earth metal salts of higher fatty acids or phenolates, for example calcium stearate, zinc stearate, magnesium stearate, sodium ricinoleate, potassium palmitate, antimony pyrocatecholate or tin pyrocatecholate, and hydroxides and oxides of alkaline earth metals or of aluminum, for example CaO, MgO and ZnO;

6. Nucleating agents, such as 4-t-butylbenzoic acid, adipic acid, diphenylacetic acid and dibenzylidenesorbitol;

7. Fillers and reinforcing agents, such as calcium carbonate, silicates, glass fibers, asbestos, talc, kaolin, mica, barium sulfate, metal oxides, metal hydroxides, carbon black and graphite;

8. Other additives, such as plasticizers, lubricants, emulsifiers, pigments, optical brighteners, flameproofing agents, antistatics and blowing agents.

The various additional additives of groups 1 to 6 above are added to the polymers to be stabilized in an amount of from 0.01 to 10% by weight, preferably from 0.01 to 5% by weight, based on the total weight of the molding composition. The amounts of the additives from groups 7 and 8 is generally from 1 to 80% by weight, preferably from 10 to 50% by weight, based on the total molding composition.

The organic polymers stabilized according to the invention can be used in various forms, for example as films, fibers, tapes, profiles or as binders for surface coatings, adhesives or putties.

In Examples 1 to 14 below, certain mixtures of solvents were used to crystallize the compounds obtained according to the invention. The data relate to ratios by volume. Optimization may be achievable by modifying the mixing ratios.

I. Examples for the Preparation of 6-aryl-6H-dibenzo[c,e][1,2]oxaphosphorines

General Procedure for Compounds of the Formula I

A Grignard compound was prepared from 300 mmol of an organobromine compound and 300 mmol (=7.3 g) of magnesium turnings in 180 ml of tetrahydrofuran under a nitrogen atmosphere and with exclusion of moisture. The resultant solution or suspension of the organometallic compound was subsequently metered over the course of 30 to 40 minutes with vigorous stirring at an internal temperature of from −20° to −10° C. into a solution of 300 mmol (=70.4 g) of 6-chloro-6H- dibenzo[c,e][1,2]oxaphosphorine in 120 ml of tetrahydrofuran/n-hexane (1:1). The reaction mixture was then allowed to warm to room temperature and was stirred for a further 2.5 hours until the reaction was complete. The precipitated magnesium salt was filtered off and washed with about 50 ml of petroleum ether, and the solvent was removed from the filtrate first under a water-pump vacuum and then under a high vacuum. The colorless or beige residue obtained was powdered and dried in a high vacuum. The product content in the crude materials was determined by $^{31}$P-NMR spectroscopy and was generally between 78 and 98% (of total P).

In the cases given, the product was crystallized from acetonitrile or acetone for characterization.

1. 6-Phenyl-6H-dibenzo[c,e][1,2]oxaphosphorine

From 47.1 g of bromobenzene, 84.8 g of a colorless resin containing 89.5% of the above compound were obtained. Crystallization from acetonitrile gave colorless crystals with a softening point of about 190° C.;
[$^{31}$P-NMR: $\delta$(CDCl$_3$)=84.1 ppm]
C$_{18}$H$_{13}$OP: 78.25 % C, 4.74 % H, 11.21% P (276.27) found: 78.0 % C, 4.5 % H, 10.9 % P.

2. 6-(2'-Tolyl)-6H-dibenzo[c,e][1,2]oxaphosphorine

From 51.3 g of o-bromotoluene, about 83 g of a colorless resin containing 93.7% of the above compound were obtained. Crystallization from acetonitrile gave colorless crystals with a melting point of 100°–102° C.
[$^{31}$P-NMR: $\delta$(CDCl$_3$)=81.8 ppm]
C$_{19}$H$_{15}$OP calc.: 78.61% C, 5.20% H, 10.66% P (290.29) found: 78.3 % C, 5.0 % H, 10.3 % P.

3. 6-(3'-Tolyl)-6H-dibenzo[c,e][1,2]oxaphosphorine

From 51.3 g of m-bromotoluene, about 86 g of a yellowish resin containing 92% of the above compound were obtained. Crystallization from acetonitrile gave colorless crystals with a melting point of 70°–75° C.
[$^{31}$P-NMR: $\delta$(CDCl$_3$)=84.5 ppm]
C$_{19}$H$_{15}$OP calc.: 78.61% C, 5.20% H, 10.66% P (290.29) found: 78.9 % C, 5.5 % H, 10.4 % P.

4. 6-(4'-Tolyl)-6H-dibenzo[c,e][1,2]oxaphosphorine

From 51.3 g of p-bromotoluene, about 83 g of a beige resin containing 94.4% of the above compound were obtained. Digestion in acetonitrile gave colorless powder with a softening point of about 60° C.
[$^{31}$P-NMR: $\delta$(CDCl$_3$)=83.6 ppm]
C$_{19}$H$_{15}$OP calc.: 78.61% C, 5.20% H, 10.66% P (290.29) found: 78.0 % C, 5.2 % H, 10.3 % P.

5. 6-(4'-Tert.-butylphenyl)-6H-dibenzo[c,e][1,2]oxaphosphorine

From 63.93 g of 4-bromo-tert.-butylbenzene, about 100 g of a yellowish, viscous resin containing 92% of the above compound were obtained. Crystallization from acetone gave colorless crystals of melting point 90°–92° C.
[$^{31}$P-NMR: $\delta$(CDCl$_3$)=83.2 ppm]
C$_{22}$H$_{21}$OP calc.: 79.49% C, 6.36% H, 9.31% P (332.38) found: 79.1% C, 6.6 % H, 9.5 % P.

6. 6-(4'-Methoxyphenyl)-6H-dibenzo[c,e][1,2]oxaphosphorine

From 56.2 g of 4-bromoanisole, about 93 g of a colorless resin containing 78% of the above compound were obtained. Crystallization from acetone gave crystals of melting point 104°–106° C.
[$^{31}$P-NMR: $\delta$(DMSO)=81.0 ppm]
C$_{19}$H$_{15}$O$_2$P calc.: 74.50% C, 4.93% H, 10.11% P (306.29) found: 74.1% C, 4.7 % H, 9.7 % P.

7. 6-(2',4',6'-Trimethylphenyl)-6H-dibenzo[c,e][1,2]oxaphosphorine

From 59.73 g of bromomesitylene, about 98 g of a yellow powder containing 84% of the above compound with a softening point of about 70° C. were obtained.
[$^{31}$P-NMR: $\delta$(CDCl$_3$)=109.9 ppm]C$_{21}$H$_{19}$OP (318.36)

8. 6-(2',3',5'-Trimethylphenyl)-6H-dibenzo[c,e][1,2]oxaphosphorine

From 59.73 g of 5-bromo-1,2,4-trimethylbenzene, about 93 g of a yellow powder with a softening point of about 70° C. and containing 98.3% of the above compound were obtained.
[$^{31}$P-NMR: $\delta$(CDCl$_3$)=81.7 ppm]
C$_{21}$H$_{19}$OP (318.36)

9. 6-(1'-Naphthyl)-6H-dibenzo[c,e][1,2]oxaphosphorine

From 62.2 g of 1-bromonaphthalene, about 90 g of a beige powder with a softening point of about 80° C. and containing 82.8% of the above compound were obtained.
[$^{31}$P-NMR: $\delta$(CDCl$_3$)=82.0 ppm]
C$_{22}$H$_{15}$OP (326.33)

10. 6-(4'-Methyl-1'-naphthyl)-6H-dibenzo[c,e][1,2]oxaphosphorine

From 66.32 g of 1-bromo-4-methylnaphthalene, about 95 g of a colorless resin containing 90% of the above compound were obtained. Crystallization from acetone gave colorless crystals of melting point 125°–127° C.
[$^{31}$P-NMR: $\delta$(CDCl$_3$)=81.7 ppm]
C$_{23}$H$_{17}$OP calc.: 81.16% C, 5.03% H, 9.09% P (340.37) found: 80.7 % C, 4.7 % H, 8.8 % P.

11. 6-(2',6'-Dimethyl-1'-phenyl)-6H-dibenzo[c,e][1,2]oxaphosphorine

From 55.5 g of 1-bromo-2,6-dimethylbenzene, about 90 g of a colorless solid containing 82% of the above compound were obtained. Crystallization from acetonitrile gave colorless crystals of melting point 93°–96° C.
[$^{31}$P-NMR: $\delta$(CDCl$_3$)=109.6 ppm]C$_{20}$H$_{17}$OP calc.: 78.93% C, 5.63% H, 10.17% P (304.32) found: 80.3 % C, 5.9 % H, 9.6 % P.

12. 6-(2',5'-Dimethyl-1'-phenyl)-6H-dibenzo[c,e][1,2]oxaphosphorine

From 55.5 g of 1-bromo-2,5-dimethylbenzene, about 88 g of a colorless resin containing 97% of the above compound were obtained. Crystallization from acetonitrile gave colorless crystals of melting point 70°–73° C.
[$^{31}$P-NMR: $\delta$(CDCl$_3$)=82.9 ppm]
C$_{20}$H$_{17}$OP calc.: 78.93% C, 5.63% H, 10.17% P (304.32) found: 78.3 % C, 5.3 % H, 9.7 % P.

13. 4,4'-Biphenylenebis{6H-dibenzo[c,e][1,2]oxaphosphorine}

In contrast to the general procedure, a Grignard compound was formed from 200 mmol (=62.4 g) of 4,4'-dibromobiphenyl and 500 mmol (=12.15 g) of magnesium turnings in 400 ml of tetrahydrofuran using ultrasound (40 kHz) and was subsequently reacted with 400 mmol (=93.9 g) of 6-chloro-6H-dibenzo[c,e][1,2]oxaphosphorine in 120 ml of tetrahydrofuran/n-hexane 1:1, giving about 105 g of a colorless solid with a softening point of 68°–70° C. and containing 73% of the above compound.
[$^{31}$P-NMR: $\delta$(CDCl$_3$)=83.4 ppm].
C$_{36}$H$_{24}$O$_2$P$_2$ (550.52)

14. 6-(1'-Naphthyl)-6H-dibenzo[c,e][1,2]oxaphosphorine

A Grignard compound was prepared from 41.4 g of 1-bromonaphthalene and 4.9 g of magnesium turnings in 150 ml of tetrahydrofuran under a nitrogen atmosphere and with exclusion of moisture. A solution of 46.9 g of 6-chloro-6H-dibenzo[c,e][1,2]oxaphosphorine in 100 ml of tetrahydrofuran was subsequently added dropwise to the resultant suspension over the course of from 30 to 40 minutes with vigorous stirring at an internal temperature of −20° C. The reaction mixture was then allowed to warm to room temperature, and was stirred for a further 2.5 hours. 150 ml of n-haptane were added, and the precipitated magnesia salt was filtered off and washed with 250 ml of n-haptane/tetrahydrofuran in the ratio 4:1. The solvent was then removed by vacuum distillation. The residue was powdered and dried in a high vacuum, giving about 65 g of a pale beige powder with a softening point of about 80° C. and containing 82.5% ($^{31}$P-NMR) of the above compound.
$C_{22}H_{15}OP$ (326.33).

II. Use Examples

The oxaphosphorines according to the invention listed below were employed for the experiments.

14: 6-(2′,4′,6′-Trimethylphenyl)-6H-dibenzo[c,e][1,2]oxaphosphorine as in Example 7, content according to $^{31}$P-NMR about 84%.

15 and 20: 6-(4′-Methoxyphenyl)-6H-dibenzo[c,e][1,2]oxaphosphorine as in Example 6

16 and 21: 6-(2′-Tolyl)-6H-dibenzo[c,e][1,2]oxaphosphorine as in Example 2

17: 6-(3′-Tolyl)-6H-dibenzo[c,e][1,2]oxaphosphorine as in Example 3

18 and 22: 6-(4′-Tert.-butylphenyl)-6H-dibenzo[c,e][1,2]oxaphosphorine as in Example 5

19: 6-(4′-Methyl-1-naphthyl)-6H-dibenzo[c,e][1,2]oxaphosphorine as in Example 10

Examples 14 to 19 and Comparative Examples A to C 100.0 g of unstabilized polypropylene powder (density: 0.903 g/cm$^3$; melt flow index MFI 230/5:4 g/10 min) were mixed with 0.1 g of calcium stearate as acid acceptor and with the amounts of phosphorus compound given in the tables, and the mixture was extruded a number of times using a bench extruder (short compression screw, screw diameter 20 mm, length 400 mm, nozzle length 30 mm, diameter 2 mm; speed: 125 rpm; temperature program: 200°/230°/230° C.). Samples were taken from the granules after the 1st and 10th passages, and the melt flow index in accordance with DIN 53 735 and the yellowing as the yellowness index in accordance with ASTM D 1925-70 were measured on these samples.

The results are shown in Tables 1 and 2.

Examples 20 to 22 and Comparative Examples D to F 100.0 g of unstabilized polypropylene powder (density: 0.903 g/cm$^3$; melt flow index MFI 230/5:4 g/10 min) were mixed with 0.1 g of calcium stearate as acid acceptor and 0.05 g of ethylene glycol bis(3,3-bis(3′-t-butyl-4′hydroxyphenyl)butyrate with the amounts of phosphorus compound given in the tables, and the mixture was extruded a number of times using a bench extruder (short compression screw, screw diameter 20 mm, length 400 mm, nozzle length 30 mm, diameter 2 mm; speed: 125 rpm; temperature program: 200°/230°/230° C.). Samples were taken from the granules after the 1st and 10th passages, and the melt flow index in accordance with DIN 53 735 and the yellowing as the yellowness index in accordance with ASTM D 1925-70 were measured on these samples. The results are shown in Tables 3 and 4.

TABLE 1

Effect of phosphorus compounds on the processing stability of polypropylene. Melt flow index MFI 230/5 after repeated granulation. (MFI in g/10 min)

| Example | Phosphorus compound | MFI after 1st | MFI after 10th granulation |
|---|---|---|---|
| Comp. A | none | 10 | 22.2 |
| Comp. B | 0.1 g of tris-(2,4-di-t-butylphenyl) phosphite | 6.4 | 10.5 |
| Comp. C | 0.1 g of tetrakis-(2,4-di-t-butylphenyl)-4,4′-biphenylene diphosphonite | 5.5 | 7.8 |
| 14 | 0.1 g of (oxaphosphorine according to the invention) | 2.1 | 7.4 |
| 15 | 0.1 g of (oxaphosphorine according to the invention) | 2.4 | 6.6 |
| 16 | 0.1 g of (oxaphosphorine according to the invention) | 2.1 | 5.8 |
| 17 | 0.1 g of (oxaphosphorine according to the invention) | 2.2 | 6.8 |
| 18 | 0.1 g of (oxaphosphorine according to the invention) | 2.2 | 6.5 |
| 19 | 0.1 g of (oxaphosphorine according to the invention) | 1.7 | 6.5 |

TABLE 2

Change in color (yellowness index in accordance with ASTM D 1925-70) on repeated granulation of polypropylene.

| Example | Phosphorus compound | YI after 1st | YI after 10th granulation |
|---|---|---|---|
| Comp. A | none | 18.7 | 27.7 |
| Comp. B | 0.1 g of tris-(2,4-di-t-butylphenyl) phosphite | 9.0 | 15.0 |
| Comp. C | 0.1 g of tetrakis-(2,4-dibutylphenyl)-4,4′-biphenyl phosphonite | 13.0 | 21.0 |
| 14 | 0.1 g of (oxaphosphorine according to the invention) | 7.0 | 21.0 |
| 15 | 0.1 g of (oxaphosphorine according to the invention) | 5.1 | 16.6 |
| 16 | 0.1 g of (oxaphosphorine according to the invention) | 4.6 | 14.6 |
| 17 | 0.1 g of (oxaphosphorine according to the invention) | 5.1 | 17.4 |
| 18 | 0.1 g of (oxaphosphorine according to the invention) | 5.7 | 15.7 |
| 19 | 0.1 g of (oxaphosphorine according to the invention) | 5.1 | 15.7 |

TABLE 3

Effect of phosphorus compounds on the processing stability of polypropylene. Melt flow index MFI 230/5 after repeated granulation. (MFI in g/10 min)

| Example | Phosphorus compound | MFI after 1st | MFI after 10th granulation |
|---|---|---|---|
| Comp. D | none | 6.3 | 14.9 |
| Comp. E | 0.05 g of tris-(2,4-di-t-butylphenyl) phosphite | 7.0 | 8.9 |
| Comp. F | 0.05 g of tetrakis-(2,4-di-t-butylphenyl)-4,4′-biphenylene diphosphonite | 5.9 | 8.9 |
| 21 | 0.05 g of (oxaphosphorine according to the invention) | 7.2 | 8.5 |
| 22 | 0.05 g of (oxaphosphorine according to the invention) | 6.5 | 10.8 |

TABLE 4

Change in color (yellowness index in accordance with ASTM D 1925-70) on repeated graunulation of polypropylene.

| Example | Phosphorus compound | YI after 1st | YI after 10th granulation |
|---|---|---|---|
| Comp. D | none | 13.7 | 35.5 |
| Comp. E | 0.05 g of tris-(2,4-di-t-butylphenyl) phopshite | 9.0 | 21.0 |
| Comp. F | 0.05 g of tetrakis-(2,4-di-t-butyl-4,4'-biphenyl phosphonite | 13.0 | 21.0 |
| 20 | 0.05 g of (oxaphosphorine according to the invention) | 8.6 | 15.0 |
| 21 | 0.05 g of (oxaphosphorine according to the invention) | 7.7 | 15.0 |
| 22 | 0.05 g of (oxaphosphorine according to the invention) | 7.3 | 9.6 |

We claim:

1. A process for the preparation of a dibenzo[c,e][1,2]-oxaphosphorine of the formula I

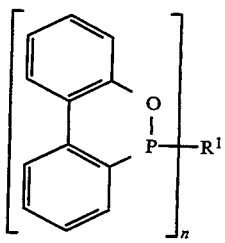

where n=1 or 2 and in which $R^1$, as a monovalent radical, is a phenyl radical, which may carry 1 to 3 substituents, or a naphthyl radical, which may carry 1 to 5 substituents, the substituents being identical or different nonaromatic hydrocarbon, alkoxy, alkylthio or dialkylamino radicals, in each case having 1 to 8 carbon atoms, aryl or aryloxy, in each case having 6 to 10 carbon atoms, or halogen having an atomic number of from 9 to 35, or, as a divalent radical, is a phenylene or biphenylene radical which is unsubstituted or substituted by up to 4 nonaromatic hydrocarbon radicals having 1 to 8 carbon atoms, or is a naphthylene radical 45 which is unsubstituted or carries 1 to 4 nonaromatic hydrocarbon radicals having 1 to 8 carbon atoms as substituents, which comprises, in a first step, reacting a hydrocarbon halide $R^1$-$(Hal)_n$ in which $R^1$ is as defined above, n=1 or 2, and the halogen has an atomic weight of at least 35, under Grignard conditions with an at least stoichiometric amount of magnesium to give the corresponding Grignard compound $R^1(MgHal)_n$, and reacting the latter, in a second step, with 6-chloro-6H-dibenzo[c,e][1,2]oxaphosphorine, forming the compound of the formula I.

2. The process as claimed in claim 1, wherein the halogen in the hydrocarbon halide is chlorine or bromine.

3. The process as claimed in claim 1, wherein the first step is carried out in an aprotic, organic solvent.

4. The process as claimed in claim 3, wherein the solvent is an ether.

5. The process as claimed in claim 1, wherein the reaction is carried out using ultrasound.

6. A dibenzo[c,e][1,2]oxaphosphorine of the formula I

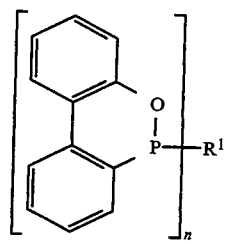

where n=1 or 2 and in which $R^1$, as a monovalent radical, is a phenyl radical, which may carry 1 to 3 substituents, or a naphthyl radical, which may carry 1 to 5 substituents, the substituents being identical or different nonaromatic hydrocarbon, alkoxy, alkylthio or dialkylamino radicals, in each case having 1 to 8 carbon atoms, aryl or aryloxy, in each case having 6 to 10 carbon atoms, or halogen having an atomic number of from 9 to 35, or, as a divalent radical, is a phenylene or biphenylene radical which is unsubstituted or substituted by up to 4 nonaromatic hydrocarbon radicals having 1 to 8 carbon atoms, or is a naphthylene radical which is unsubstituted or carries 1 to 4 nonaromatic hydrocarbon radicals having 1 to 8 carbon atoms as substituents.

7. A process for the preparation of a stabilized plastic material comprising the step of incorporating from 0.01 to 10% by weight of a compound of the formula

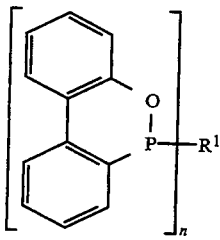

into a plastic material where n=1 or 2 and in which $R^1$, as a monovalent radical, is a phenyl radical, which optionally carries 1 to 3 substituents, or a naphthyl radical, which optionally carries 1 to 5 substituents, the substituents being identical or different nonaromatic hydrocarbon, alkoxy, alkylthio or dialkylamino radicals, in each case having 1 to 8 carbon atoms, aryl or aryloxy, in each case having 6 to 10 carbon atoms, or halogen having an atomic number of from 9 to 35, or, as a divalent radical, is a phenylene or biphenylene radical which is unsubstituted or substituted by up to 4 nonaromatic hydrocarbon radicals having 1 to 8 carbon atoms, or is a naphthylene radical which is unsubstituted nonaromatic hydrocarbon radicals having 1 to 8 carbon atoms as substituents.

8. A process for the preparation of a stabilized plastic material comprising the step of incorporation of a compound of the formula

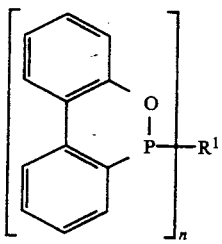

into a plastic material, said compound being incorporated in a concentration of 1 to 50% by weight where n=1 or 2 and in which $R^1$, as a monovalent radical, is a phenyl radical, which optionally carries 1 to 3 substituents, or a naphthyl radical, which optionally carries 1 to 5 substituents, the substituents being identical or different nonaromatic hydrocarbon, alkoxy, alkylthio or dialkylamino radials, in each case having 1 to 8 carbon atoms, aryl or aryloxy, in each case having 6 to 10 carbon atoms, or halogen having an atomic number of from 9 to 35, or, as a divalent radical, is a phenylene or biphenylene radical which is unsubstituted or substituted by up to 4 nonaromatic hydrocarbon radicals having 1 to 8 carbon atoms, or is a naphthylene radical which is unsubstituted nonaromatic hydrocarbon radicals having 1 to 8 carbon atoms as substituents.

9. A process according to claim 8 further comprising the steps of incorporating a phenolic antioxidant into a plastic.

10. A process according to claim 8, wherein the plastics are polymerization plastics.

11. A composition as claimed in claim 8, wherein the abc ratio is (98 to 99.95):(0.025 to 1):(0.025 to 1) % by weight.

12. A plastic molding composition comprising from 90 to 99.99% by weight of the composition of a thermoplastic or thermoset resin and from 0.01 to 10% by weight (of the composition) of a dibenzo[c,e][1,2]oxaphosphorine of the formula

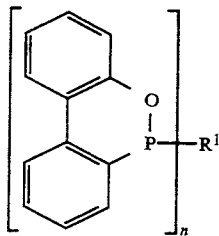

(I)

where n=1 or 2 and in which $R^1$, as a monovalent radical, is a phenyl radical, which optionally carries 1 to 3 substituents, or a naphthyl radical, which optionally carries 1 to 5 substituents, the substituents being identical or different nonaromatic hydrocarbon, alkoxy, alkylthio or dialkylamino radicals, in each case having 1 to 8 carbon atoms, aryl or aryloxy, in each case having 6 to 10 carbon atoms, or halogen having an atomic number of from 9 to 35, or, as a divalent radical, is a phenylene or biphenylene radical which is unsubstituted or substituted by up to 4 nonaromatic hydrocarbon radicals having 1 to 8 carbon atoms, or is a naphthylene radical which is unsubstituted or carries 1 to 4 nonaromatic hydrocarbon radicals having 1 to 8 carbon atoms as substituents.

13. A plastic molding composition as claimed in claim 12 wherein the plastic is a polyolefin.

14. A plastic molding composition as claimed in claim 12 additionally containing antioxidants, UV absorbers, light stabilizers, metal deactivators, peroxide-destroying compounds, basic costabilizers, nucleating agents, fillers, reinforcing agents, plasticizers, lubricants, emulsifiers, pigments, optical brighteners, flameproofing agents, antistatics or blowing agents.

15. A plastic molding composition as claimed in claim 12, wherein the plastic is polypropylene.

16. A plastic molding composition as claimed in claim 12 or 13 comprising
 a) the thermoplastic or thermoset resin,
 b) said phosphonite and
 c) an ester of $C_1$) the 3,3-bis(3'-t-butyl-4'-hydroxyphenyl) butanoic acid of the formula II

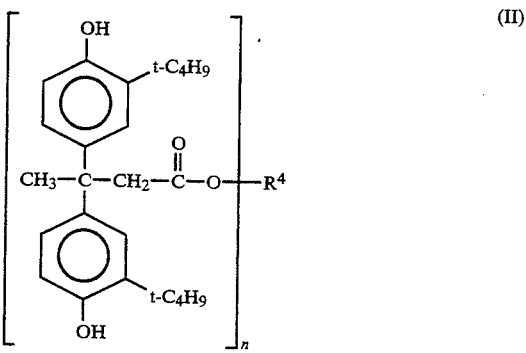

in which n is 1 or 2 and $R^4$ is a $C_1$ to $C_{12}$-alkyl radical if n is 1 or is a $C_1$ to $C_{12}$-alkylene radical if n is 2, or of $C_2$) the β-(3,5-di-t-butyl-4-hydroxyphenyl)propionic acid of the formula III

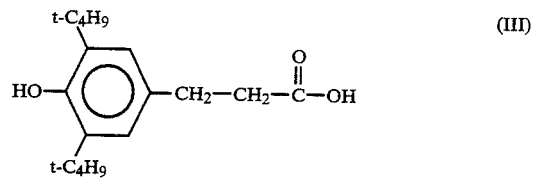

with a monohydric to tetrahydric alcohol,
 in an a:b:c ratio of (90 to 99.98):((0.01 to 5):(0.01 to 5) % by weight.

* * * * *

UNITED STATES PATENT AND TRADEMARK OFFICE
CERTIFICATE OF CORRECTION

PATENT NO. : 5,356,967
DATED : October 18, 1994
INVENTOR(S) : Manfred Böhshar, et al It is certified that error appears in the above-indentified patent and that said Letters Patent is hereby corrected as shown below:

Claim 7, column 16, line 62, after "unsubstituted" insert -- or carries 1 to 4 --.

Claim 8, column 17, line 26, after "unsubstituted" insert -- or carries 1 to 4 --.

Claim 11, column 17, line 33, delete "claim 8," and replace with -- claim 12 --.

Signed and Sealed this

Twenty-first Day of February, 1995

Attest:

BRUCE LEHMAN

*Attesting Officer*  *Commissioner of Patents and Trademarks*